United States Patent [19]

Scott

[11] Patent Number: 6,139,709
[45] Date of Patent: Oct. 31, 2000

[54] APPARATUS FOR PRODUCING ELECTROPHORESIS GELS

[75] Inventor: Charles B. Scott, Rancho Santa Fe, Calif.

[73] Assignee: C.B.S. Scientific Co., Inc., Del Mar, Calif.

[21] Appl. No.: 09/033,388

[22] Filed: Mar. 2, 1998

[51] Int. Cl.[7] .................................................. G01N 27/26
[52] U.S. Cl. ........................ 204/619; 204/615; 249/134
[58] Field of Search ..................................... 204/606, 615, 204/616, 618, 619, 620; 71/64.04; 435/397; 99/432, 426, 430, 431; 249/117, 134

[56] References Cited

U.S. PATENT DOCUMENTS 4,035,377  7/1977  Detroy ..................................... 204/619
5,324,412  6/1994  Kolner .................................... 204/619

Primary Examiner—T. Tung
Assistant Examiner—Alex Noguerola
Attorney, Agent, or Firm—James C. Weseman, Esq.; The Law Offices of James C. Weseman

[57] ABSTRACT

A device and apparatus for producing ultra-thin electrophoresis gels formed between spaced-apart plates is provided, where at least one of the plates has a plurality of grooves, the device comprising a spacer comb having extensions formed thereon which are arranged, sized, shaped and located so as to approximately mate with and occupy the grooves on the plate so as to exclude gel material from the grooves during the formation of the electrophoresis gel.

3 Claims, 2 Drawing Sheets

APPARATUS FOR PRODUCING ELECTROPHORESIS GELS

TECHNICAL FIELD

The present invention relates to devices for the electrophoretic separation of molecules, and, more particularly, to the creation and use of extremely thin electrophoresis gels for such separation.

BACKGROUND OF THE INVENTION

Electrophoresis is the process of separating molecules on the basis of the molecule's migration through a gel in an applied electric field. In an electric field, a molecule will migrate towards the pole that carries a charge opposite to the net charge carried by the molecule. This net charge depends in part on the pH of the medium in which the molecule is migrating.

One common electrophoretic procedure is to establish solutions having different pH values at each end of an electric field, with a gradient range of pH in between. At a certain pH, the isoelectric point of a molecule is obtained and the molecule carries no net charge. Therefore, as the molecule crosses the pH gradient, the molecule reaches an isoelectric point and is immobile in the electric field. Therefore, this electrophoresis procedure separates molecules according to their different isoelectric points.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by both molecular size and isoelectric point.

Electrophoresis in a polymeric gel can also be used to separate molecules, such as RNA and DNA molecules, all have the same isoelectric point. These groups of molecules will migrate through an electric field across a polymeric gel on the basis of molecular size. Molecules with different isoelectric points, such as proteins, can be denatured in a solution of detergent, such as sodium dodecyl sulfate (SDS). The SDS-covered proteins will have similar isoelectric points and will migrate through the gel on the basis of molecular size. The separation of DNA molecules on the basis of their molecular size is an important step in determining the nucleotide sequence of a DNA molecule.

A polymeric gel electrophoresis system is typically set up in the following way: A gel-forming solution is allowed to polymerize between two glass plates that are held apart on two sides by spacers. These spacers determine the thickness of the gel. Typically, sample wells are formed by inserting a comb-shaped mold into the liquid between the glass plates at one end and allowing the liquid to polymerize around the mold. Alternatively, the gel may be cast with a flat top and a pointed comb inserted between the plates so that the points are slightly imbedded in the gel. Small, fluid-tight areas between the points can be filled with a sample.

The top and bottom of the polymerized gel are placed in electrical contact with two buffer reservoirs. Macromolecule samples are loaded into the sample wells. A sample-loading implement, such as a pipette, is inserted between the two glass plates and the sample is injected into the well. To prevent sample mixing, it is advantageous to inject the sample as close to the gel as possible. It is difficult to place the tip of the pipette or loading implement close to the gel because the pipette tip is often wider than the gel.

An electric field is set up across the gel, and the molecules begin to move into the gel and separate according to their size. The size-sorted molecules can be visualized in several ways. After electrophoresis, the gels can be bathed in a nucleotide-specific or protein-specific stain which renders the groups of size-sorted molecules visible to the eye. For greater resolution, the molecules can be radioactively labeled and the gel exposed to X-ray film. The developed X-ray film will indicate the migration positions of the labeled molecules.

Both vertical and horizontal assemblies are routinely used in gel electrophoresis. In a vertical apparatus, the sample wells are formed in the same plane as the gel and are loaded vertically. The wells can be as deep and wide as needed, but the thickness of the well is limited by the thickness of the gel.

Thin electrophoresis gels (less than approximately 1.0 mm) and ultra-thin gels (less than approximately 0.2 mm) have been found to be useful because they may be subjected to a higher voltage than thicker gels during electrophoresis. Therefore, the electrophoretic procedure will run faster. Another advantage of thin and ultra-thin gels is higher resolution because less sample is needed. Because of their thinness, the ultra-thin gels are fixed for autoradiography quickly and easily.

The problem of sample loading is especially burdensome with ultra-thin gel electrophoresis. The dimensions of the sample well are usually determined by the thickness of the gel. Therefore, ultra-thin gels have ultra-thin sample wells. As a practical matter it is difficult to load gels less than 1 mm thickness with a conventional pipette or less than 0.2 mm in thickness with a capillary tube. Sample loading can be accomplished using very thin, flat pipette tips or pulled glass capillaries to deposit samples into the wells. However, viscous samples are difficult to pipette with these loading devices because the devices can clog and break readily.

In order to address this problem, U.S. Pat. No. 5,324,412 discloses a device that enables easier loading of ultra-thin electrophoretic gels. This device consists of a grooved glass plate as one of the spaced-apart plates in the formation of the gel. These plate grooves are intended to be aligned with the sample wells to permit more convenient access to the well with a sample loading device. However, it has been found that in the process of forming the gel the grooves are typically clogged with gel resin, and require extensive cleaning in order to restore their intended function.

Thus, it is considered desirable to provide a means for preventing clogging of the access grooves during the formation of thin and ultra-thin electrophoresis gels.

DISCLOSURE OF THE INVENTION

The present invention provides a device for producing thin and ultra-thin electrophoresis gels formed between spaced-apart plates, where at least one of the plates has a plurality of grooves, the device comprising a spacer comb having extensions formed thereon which are arranged, sized, shaped and located so as to approximately mate with and occupy the grooves on the plate so as to exclude gel material from the grooves during the formation of the electrophoresis gel.

In another aspect, the invention provides an apparatus for forming electrophoresis gels comprising a back plate and a front plate, where at least one of the plates has a plurality of extended grooves, and the plates are arranged so that the grooves face toward the remaining plate. Also included is at least one spacer located between the plates and in contact with each of them so that the spacer defines the distance between the plates, the spacer and the plates defining a gel mold therebetween. A spacer comb is then located between the plates, corresponding in thickness to the approximate thickness of the spacer, the spacer comb having extensions formed thereon which are arranged, sized, shaped and located so as to approximately mate with and occupy the grooves on the plate so as to exclude gel material from the grooves during the formation of the electrophoresis gel.

DETAILED DESCRIPTION OF THE INVENTION

The present invention provides a device for producing thin and ultra-thin electrophoresis gels formed between spaced-apart plates, where at least one of the plates has a plurality of grooves, the device comprising a spacer comb having extensions formed thereon which are arranged, sized, shaped and located so as to approximately mate with and occupy the grooves on the plate so as to exclude gel material from the grooves during the formation of the electrophoresis gel.

In another aspect, the invention provides an apparatus for forming electrophoresis gels comprising a back plate and a front plate, where at least one of the plates has a plurality of extended grooves, and the plates are arranged so that the grooves face toward the remaining plate. Also included is at least one spacer located between the plates and in contact with each of them so that the spacer defines the distance between the plates, the spacer and the plates defining a gel mold therebetween. A spacer comb is then located between the plates, corresponding in thickness to the approximate thickness of the spacer, the spacer comb having extensions formed thereon which are arranged, sized, shaped and located so as to approximately mate with and occupy the grooves on the plate so as to exclude gel material from the grooves during the formation of the electrophoresis gel.

The present invention is intended to be utilized in conjunction with electrophoresis gel-forming apparatus, such as the apparatus disclosed in U.S. Pat. No. 5,324,412, the entire contents of which are incorporated by this reference. As disclosed therein, thin and ultra-thin electrophoresis gels can be formed by utilizing at least one plate with grooves provided in the gel-loading end of the plate, most commonly in a vertical gel device. These grooves are then vertically oriented and aligned with sample-holding wells in the gel and allow one to more easily inject sample with a sample-loading implement, such as a pipette or a capillary tube, into the well.

This arrangement of grooves and gel is intended to allow the gel to be more easily loaded. However, it has been discovered that the grooves will typically clog with gel during the formation procedure, and require time-consuming and costly cleaning before use.

Figure 1:
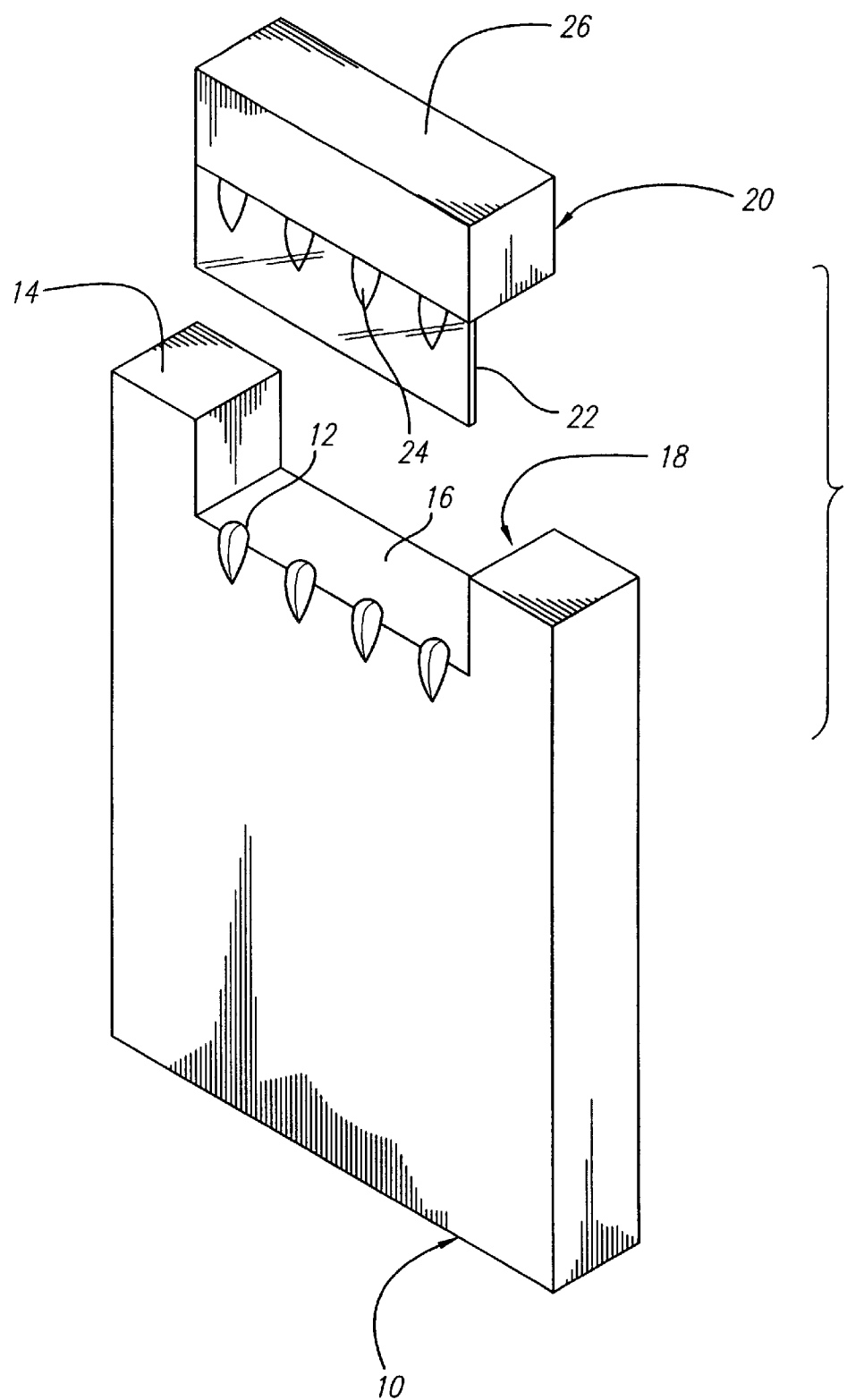
FIG. 1 is a perspective view of a plate used to form thin and ultra-thin electrophoresis gels in accordance with the prior art and the device of the present invention with portions in phantom line.
Figure 2:
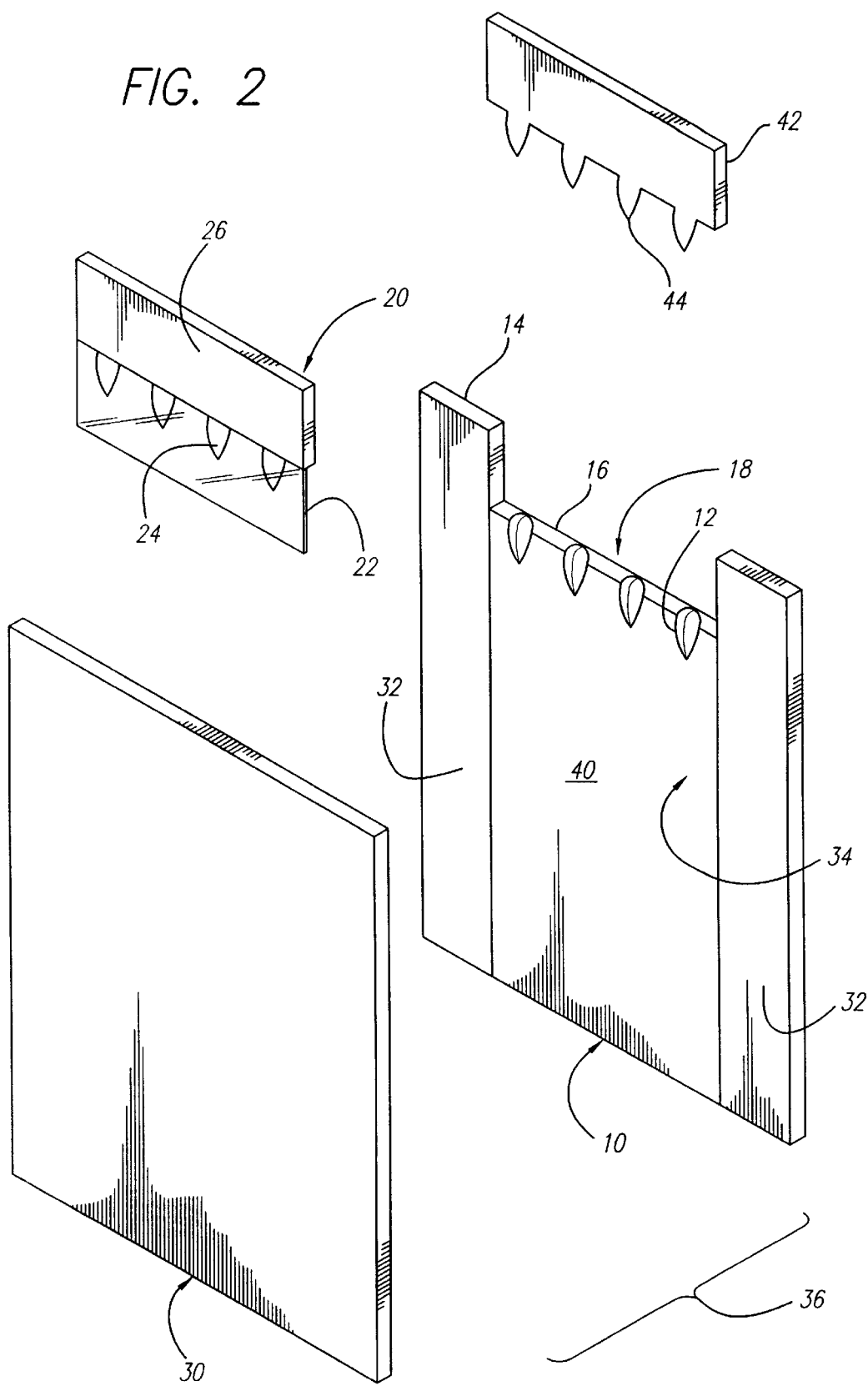
FIG. 2 is a exploded perspective view of an embodiment of the device and apparatus of the present invention used to form thin and ultra-thin electrophoresis gels.

FIGS. 1 and 2 depict the structure of one embodiment of the present invention. FIG. 1 is a diagram of a plate for an electrophoresis gel forming apparatus in accordance with the prior art, together with an embodiment of the present device. The present device and apparatus, with the plate of FIG. 1 included, is illustrated at FIG. 2.

Referring to FIG. 1, a plate 10 contains grooves 12 at the sample-loading end 14 of the plate 10. Plate 10 is typically formed of glass. The grooves 12 can be formed at the same time as the plate, but are more typically ground into the inside upper edge 16 of notch portion 18 of plate 10 using a grinding implement such as a Dremel® Moto-Tool (Dremel, Racine, Wis.) and an oval shaped silicon carbide grinding stone (#84922), utilizing a template to maintain the pattern. Preferably the grooves 12 are conical in shape, vertically extending with a downward taper, although other geometries are suitable. The grooves should be sized and arranged to correspond to the size of the sample wells which are intended to be established in the gel, and to the size of the loading pipette tip. A conical shape is preferable because the sample will be funneled toward and collect at the small end of the groove before moving into the gel. As an alternative to a plate 10 having notch portion 18, the plate 10 can be a rectangular plate and grooves 12 will be provided at one end thereof.

Also depicted in FIG. 1 is an embodiment of the spacer comb device of the present invention. Spacer comb 20 will include spacer portion 22, typically formed of non-conductive material capable of forming a water-tight seal, such as polyester or mylar, having extensions 24 formed thereon, typically formed of a pliable material molded onto the spacer portion 22, and also capable of forming a water-tight seal. The extensions 24 are arranged, sized, shaped and located so as to approximately mate with and occupy the grooves 12 on the plate 10, so as to exclude gel material from the grooves during the formation of the electrophoresis gel. Spacer comb 20 will also typically include a handle portion 26 which approximates the dimensions of the notch portion 18 of plate 10. This handle portion 26 will increase the rigidity of the spacer comb 20 device during use, and facilitate its removal after the gel has been formed.

The use of the present device will be more clearly explained by reference to FIG. 2, in which the assembled apparatus of the invention is depicted in exploded perspective view. FIG. 2 depicts the arrangement of plates 10 and 30 in a typical vertical electrophoresis apparatus. Many other versions of this apparatus exist. In the present apparatus, two plates 10 and 30 are matched so that, when brought together they will form two sides of a gel formation chamber. Spacers 32, typically formed of non-conductive material capable of forming a water-tight seal, such as polyester or mylar, are placed against the front sides of plate 10 and the back sides of plate 30. Where plate 10 is rectangular, spacers 32 will be configure to fit along the side of plate 10 as well as between plates 10 and 30.

Referring to FIG. 2, the present apparatus is composed of plates 10 and 30, spacers 32, and spacer comb 20, assembled to form a plate assembly 36 enclosing a gel-forming chamber 34 for receiving the selected liquid gel and holding it while the gel solidifies. Typically, plate 30 is the front plate while plate 10 is the back plate, reference being made to when the apparatus is assembled onto an electrophoresis apparatus as described below. The two plates are assembled with spacer 32 between them, and pressed together with the spacer in between. Thus the spacer 32 defines the distance between the plates. The plates 10 and 30 and the spacer 32 define a gel chamber 34 into which the electrophoresis gel can be poured to be polymerized or solidified in place. Thus the polymeric gel 40 occupies the space in the gel chamber between the plates 10 and 30 and spacers 32.

Thin and ultra-thin gels (including those typically less than 0.2 mm) can be formed in many ways. For example, forming an ultra-thin gel using grooved plate 10 for radioactive DNA, sequence analysis may comprise the following steps: Plate 10 is coated with gamma-methacryloxypropyltrimethoxysilane (Sigma, St. Louis, Mo.) before the gel 40 is formed to covalently bind gel 40 to plate 10. Plate 30 is treated with a siliconizing agent (Surfasil, Pierce, Rockford, Ill.) to prevent sticking of gel 40. The plates 30 and 10 are clamped together with spacers 32 and placed horizontally on a support, such as an empty ice bucket. A polyacrylamide gel solution is prepared and poured between plates 30 and 10. Spacer comb 20 is provided, where spacer portion 22 is typically constructed from the same material as the spacers 32 and is inserted into the space between plates 30 and 10, with the extensions 24 matching the grooves 12 and the handle portion 26 conforming to notch portion 18 of plate 10. The presence of spacer comb 20 also prevents oxygen from contacting the polyacrylamide solution and, thus, the gel can polymerize.

In assembling the present apparatus for use in an electrophoresis system, an number of additional components are commonly used in the prior art. For example, a supporting base is typically employed, in which an upper buffer solution vessel and a lower buffer solution vessel are mounted on the supporting base. An upper electrode and a lower electrode, each typically formed of a single platinum wire extending the width of the apparatus, are respectively disposed in the upper buffer solution vessel and the lower buffer solution vessel, so that the electrodes are dipped in a buffer solution contained in the vessels. The electrodes are connected to external terminals, which project outwardly from the sidewalls of the vessels.

The upper buffer solution vessel is usually constructed of plastic, commonly plexiglass, and defined by side plates, a rear and bottom plate and a front frame. A cut-away portion is formed at the upper section of the front frame, which is typically dimensioned to match the notch portion 18 of plate 10.

In assembling the present apparatus into an electrophoresis system, plate assembly 36 is fitted to the front side of the electrophoresis support front frame and clamped to the sides of the frame, and spacer comb 20 is removed. As a result, the electrophoresis plate assembly 36 closes the cut-away portion in the front surface of the upper buffer solution vessel, while allowing the buffer to contact the gel 40, via the notch portion 18 of plate 10, or the equivalent region on an un-notched plate. After buffer has been added to the upper buffer chamber and lower buffer chamber, a comb 42 is inserted between plates 30 and 10. The teeth 44 of the comb 42 are then slightly imbedded into gel 40. The spaces that form between the teeth 44 and the top of the gel 40 are aligned with grooves 12 such that the teeth 44 are on either side of the individual grooves 12. These spaces formed between the teeth 44 and gel 40 are to be filled with sample. The grooves 12, kept unobstructed by the use of spacer comb 20 during the formation of the gel, allow a sample-loading implement to more easily inject a sample into the spaces between the teeth 44 and the top of the gel 40. After the samples are loaded, current is applied to the system from a current generator through the external terminals, and the sample in each well will migrate into the gel.

The grooved vertical electrophoresis plate 10 circumvent the difficulties associated with loading samples into thin and ultra-thin gels, and the use of the present spacer comb 20 prevents obstruction of the grooves during the formation of the gel 40. The grooves 12 allow a conventional pipette tip (approximately 1 mm thick) to be inserted between plates 30 and 10. Plates 30 and 10 are preferably spaced at least 0.070 mm apart, and up to approximately 1.0 mm apart. More generally, plates 30 and 10 are spaced less than approximately 0.2 mm apart. The unobstructed grooves 12 funnel the sample into the middle portion of the well, where the higher density of the sample loading buffer brings it to the gel interface. This arrangement simplifies loading and, thus, running of thin and ultra-thin gels.

In the operation of an electrophoresis system, appropriate electrophoresis times vary with the thickness of gel. A 0.075 mm gel that is 40 cm by 16 cm and composed of 6% polyacrylamide/5% bisacrylamide/8M urea may be run at 40 watts constant power (110–135 volts per cm gel) for 30 minutes for a bromphenol blue marker to travel the length of the gel.

At the end of the electrophoretic run, plate 30 is separated away from plate 10.

The gel 40 which was covalently bound to plate 10 is fixed with a 10% acetic acid/10% methanol solution for 2 minutes and rinsed thoroughly with water. Gel 40 is then dried, typically in less than 15 minutes, by placing the plate on a aluminum surface heated to about 70° C. with a laboratory hot plate. Since gel 40 remains attached to plate 10, it is not damaged by handling. Autoradiography is performed at room temperature.

Most commercially available sequencing apparatus can be adapted to use the device and apparatus of the present invention. Moreover, the use of this improvement readily permits use of conventional pipette both to load samples in thin gels (less than 1 mm) and in ultra-thin gels (less than 0.2 mm). The grooves which are used to help define the sample loading wells can be formed in either or both of the plates of the apparatus and can readily be retrofit into existing equipment.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

What is claimed is:

1. A device for forming sample well access channels in an electrophoresis gel which is formed between spaced-apart plates, at least one of the plates having formed in it a plurality of grooves, said device comprising a spacer comb corresponding in thickness to the approximate thickness of the electrophoresis gel, the spacer comb having extensions formed thereon which are arranged, sized, shaped and located so as to approximately mate with and occupy the grooves on the plate so as to exclude gel material from the grooves during the formation of the electrophoresis gel.

2. The device of claim 1 wherein said grooves are conical in cross section.

3. An apparatus for forming electrophoresis gels comprising a back plate and a front plate, at least one of the plates having formed in it a plurality of extended grooves, and said plates arranged so that the grooves face toward the remaining plate;

at least one spacer located between the front plate and the back plate and in contact with each of them so that the spacer defines the distance between the plates, the spacer and the plates defining a gel mold therebetween; and a spacer comb located between the front plate and the back plate and corresponding in thickness to the approximate thickness of the spacer, the spacer comb having extensions formed thereon which are arranged, sized, shaped and located so as to approximately mate with and occupy the grooves on the plate so as to exclude gel material from the grooves during the formation of the electrophoresis gel.

* * * * *